United States Patent
Lin et al.

(10) Patent No.: US 10,783,359 B2
(45) Date of Patent: Sep. 22, 2020

(54) HEADSET WITH MOTION SENSOR

(71) Applicant: Merry Electronics(Shenzhen) Co., Ltd., ShenZhen (CN)

(72) Inventors: Meng-Wei Lin, Taichung (TW); Mao-Hung Lin, Taichung (TW); Hung-Chi Lin, Taichung (TW); Sheng Chen, Taichung (TW)

(73) Assignee: Merry Electronics (Shenzhen) Co., Ltd., ShenZhen (CN)

( * ) Notice: Subject to any disclaimer, the term of this patent is extended or adjusted under 35 U.S.C. 154(b) by 0 days.

(21) Appl. No.: 16/293,660

(22) Filed: Mar. 6, 2019

(65) Prior Publication Data

US 2020/0169802 A1 May 28, 2020

(30) Foreign Application Priority Data

Nov. 27, 2018 (TW) .............................. 107142162 A

(51) Int. Cl.

| | |
|---|---|
| *G06K 9/00* | (2006.01) |
| *G06F 3/16* | (2006.01) |
| *G06F 3/01* | (2006.01) |
| *A61B 5/11* | (2006.01) |
| *A63B 23/02* | (2006.01) |
| *A61B 5/00* | (2006.01) |
| *H04R 1/10* | (2006.01) |
| *H04R 5/033* | (2006.01) |
| *G08B 21/04* | (2006.01) |

(52) U.S. Cl.
CPC ........ *G06K 9/00335* (2013.01); *A61B 5/1116* (2013.01); *A61B 5/4561* (2013.01); *A63B 23/0244* (2013.01); *G06F 3/011* (2013.01); *G06F 3/012* (2013.01); *G06F 3/167* (2013.01); *A63B 2208/02* (2013.01); *A63B 2230/62* (2013.01); *G08B 21/0446* (2013.01); *H04R 1/1016* (2013.01); *H04R 5/033* (2013.01); *H04R 5/0335* (2013.01); *H04R 2430/01* (2013.01)

(58) Field of Classification Search
CPC .......... G06F 3/167; G06F 3/011; G06F 3/012; G06K 9/00335; G06K 9/00342; H04R 1/1016; H04R 5/033; H04R 5/0335; H04R 2430/01; A63B 23/0244; A63B 2208/02; A63B 2230/62; A61B 5/1116; A61B 5/4561; G08B 21/0446
USPC .......................................................... 700/94
See application file for complete search history.

(56) References Cited

U.S. PATENT DOCUMENTS

| | | | | |
|---|---|---|---|---|
| 6,209,011 B1 * | 3/2001 | Vong | ...................... | G04G 11/00 708/112 |
| 8,428,758 B2 * | 4/2013 | Naik | ...................... | G10L 21/00 381/107 |
| 2013/0207889 A1 * | 8/2013 | Chang | .................. | A61B 5/0002 345/156 |
| 2017/0325718 A1 * | 11/2017 | Boesen | ................ | A61B 5/1101 |

(Continued)

*Primary Examiner* — Jesse A Elbin
(74) *Attorney, Agent, or Firm* — JCIPRNET

(57) ABSTRACT

A headset including a speaker, a motion sensor, a transceiver, and a processor is provided. The speaker plays audio data. The motion sensor senses a posture of a user to generate first sensing data. The transceiver performs data transmission with an external device. The processor is coupled to the motion sensor and the transceiver. The processor determines whether the posture is correct according to the first sensing data to generate an output result and transmits the output result through the transceiver.

12 Claims, 5 Drawing Sheets

(56) References Cited

U.S. PATENT DOCUMENTS

| | | | | |
|---|---|---|---|---|
| 2018/0005395 A1* | 1/2018 | D'Angelo | ............. | G06T 1/0007 |
| 2018/0164983 A1* | 6/2018 | Torii | ......................... | G06F 3/14 |
| 2018/0288516 A1* | 10/2018 | Perry | ...................... | G06F 3/167 |
| 2018/0321906 A1* | 11/2018 | Laaksonen | .............. | G06F 3/017 |
| 2019/0380597 A1* | 12/2019 | Howard | ............... | H04R 25/652 |

* cited by examiner

HEADSET WITH MOTION SENSOR

CROSS REFERENCE TO RELATED APPLICATION

This application claims the priority benefit of Taiwan application serial no. 107142162, filed on Nov. 27, 2018. The entirety of the above-mentioned patent application is hereby incorporated by reference herein and made a part of specification.

BACKGROUND

Technical Field

The invention relates to a headset. More particularly, the invention relates to a headset with a motion sensor.

Description of Related Art

Along with technology advancement, a large number of smart mobile accessories matched with motion sensors, such as smart bracelets, smart watches and the like, have hit the market. In the accessories of these types, data sensed by the motion sensors is transmitted to smartphones through wireless transmission technology, the data is analyzed through apps in the smartphones, and analysis results are then generated. A user may obtain information associated with physiological conditions and motion conditions such as the personal heart rhythm and motion steps through the analysis results. Nevertheless, wireless transmission consumes a large amount of power in the smart mobile accessories and smartphones, and further, poor connection quality may delay the analysis of the data as well.

From another perspective, as regards an identification model used to analyze the sensing data associated with a motion posture, a large amount of label data is required to be used most of the time when the identification model is trained. Generally, the label data is generated by the person who labels the sensing data according to his/her own determination of the posture. When data labeling is manually performed, efficiency in data labeling is not great. In addition, different people have different determination standards of the same posture, and further, people may feel tired during a long process of labeling, so determination errors may occur. As such, the label data used to train the model is often mixed with many pieces of incorrect label data, so performance of the model may be unfavorable.

SUMMARY

The invention provides a headset capable of improving the problem of significant power consumption in a headset with a motion sensor and overcoming data analysis delay caused by poor connection quality.

A headset provided by an embodiment of the invention includes a speaker, a motion sensor, a transceiver, and a processor. The speaker plays audio data. The motion sensor senses a posture of a user to generate first sensing data. The transceiver performs data transmission with an external device. The processor is coupled to the motion sensor and the transceiver. The processor determines whether the posture is correct according to the first sensing data to generate an output result and transmits the output result through the transceiver.

A headset provided by an embodiment of the invention includes a speaker, a motion sensor, and a processor. The speaker plays audio data. The motion sensor senses a posture of a user to generate first sensing data. The processor may include a data processing unit and an audio processing unit, and the data processing unit is coupled between the motion sensor and the audio processing unit. The data processing unit determines whether the posture is correct according to the first sensing data to generate an output result and transmits the output result through the audio processing unit to the speaker for playing.

To sum up, the headset provided by the invention is capable of transmitting original data generated by the sensor to the external device such as a smartphone and the like without the use of wireless transmission technology. Therefore, power consumed by the headset and/or the external device is significantly lowered.

The invention provides a system and a method for generating label data in order to increase efficiency in generating label data and to improve identification accuracy of a trained model.

A system for generating label data provided by an embodiment of the invention includes a first image capturing device, a second image capturing device, a motion sensing device, and a first processor. The first image capturing device may sense a posture of a user to generate a non-depth image. The second image capturing device may sense the posture of the user to generate a depth image. The motion sensing device senses the posture of the user to generate motion data. The first processor is coupled to the first image capturing device, the second image capturing device, and the motion sensing device. The first processor generates an identifying result of the posture according to the non-depth image and the depth image and labels the motion data according to the identification result to generate label data.

A method for generating label data provided by an embodiment of the invention includes the following steps. A posture of a user is sensed to generate a non-depth image. The posture of the user is sensed to generate a depth image. The posture of the user is sensed to generate motion data. An identifying result of the posture is generated according to the non-depth image and the depth image, and the motion data is labeled according to the identification result to generate label data.

To sum up, the system for generating label data provided by the invention can automatically perform data labeling and help the user to generate the label data more quickly, and moreover, identification accuracy of the identification model trained by using the label data is increased as well.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
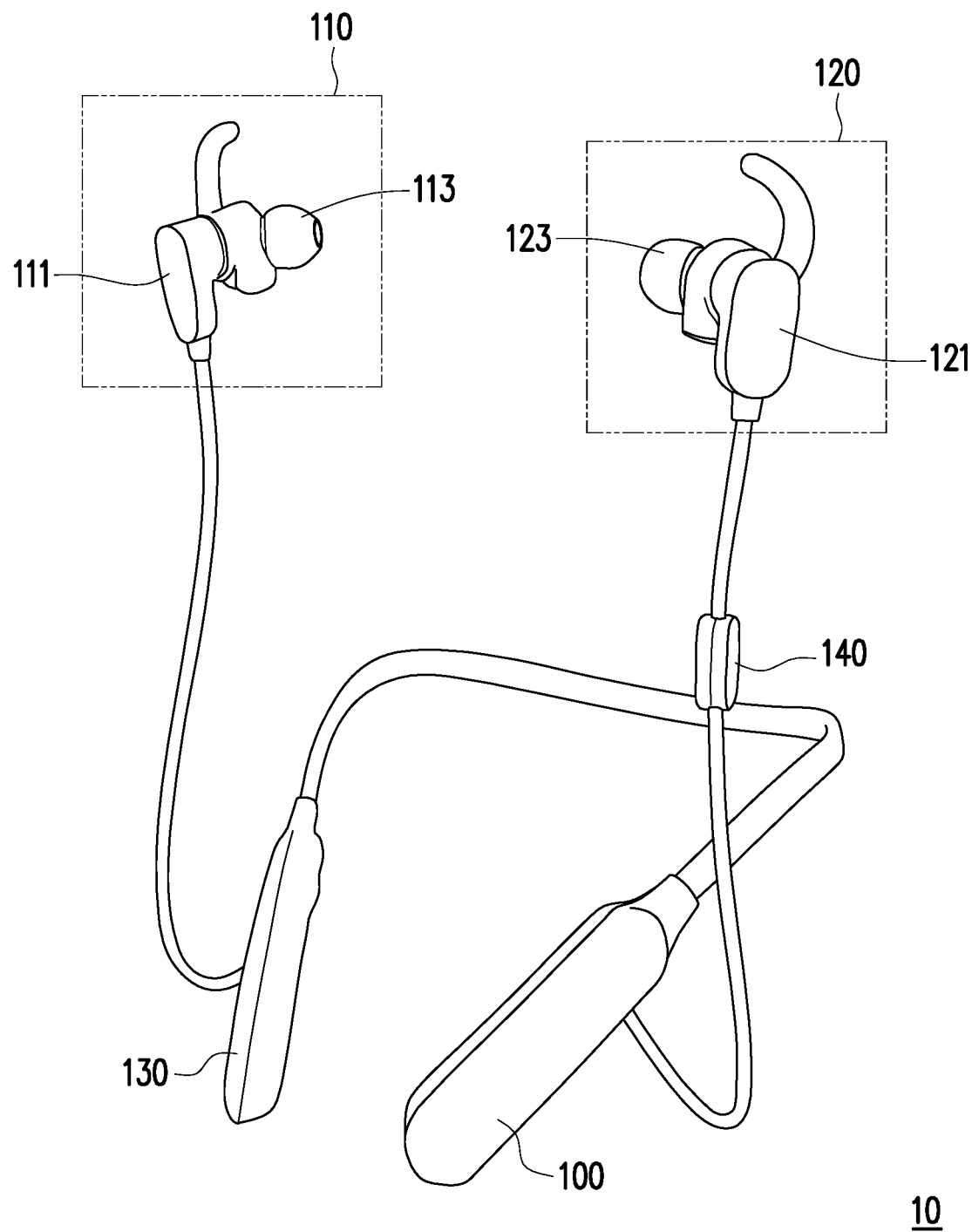
FIG. 1 is a schematic view illustrating a headset according to an embodiment of the invention.
Figure 2:
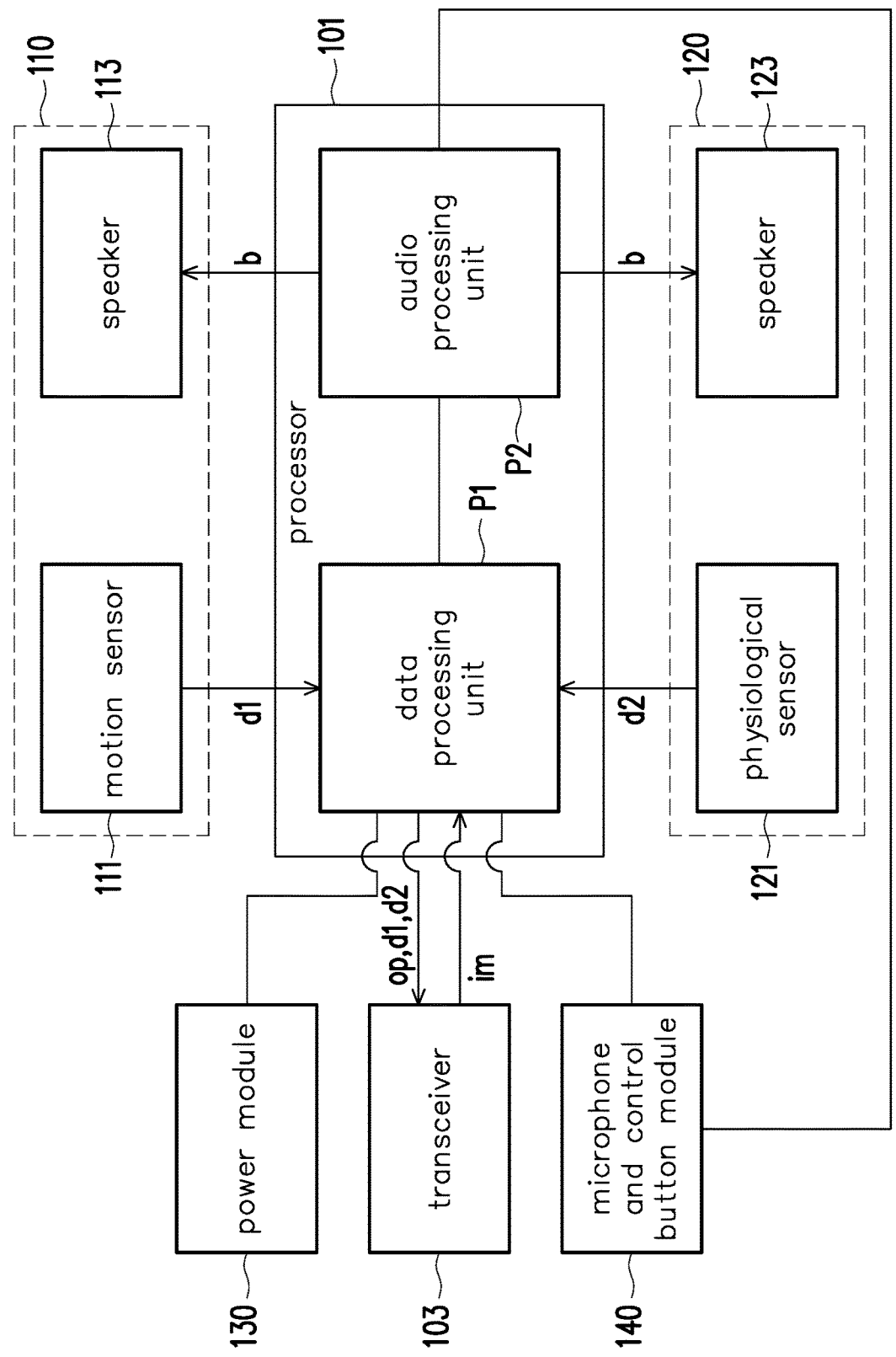
FIG. 2 is a block diagram illustrating functions of the headset according to an embodiment of the invention.

FIG. 1 is a schematic view illustrating a headset 10 according to an embodiment of the invention, and FIG. 2 is a block diagram illustrating functions of the headset 10 according to an embodiment of the invention. The following refers to FIG. 1 and FIG. 2 together.

The headset 10 may include a main board 100, a first housing 110, a second housing 120, a power module 130, and a microphone and control button module 140. The power module 130 is configured to provide power required to be consumed by the headset 10 to operate. The microphone and control button module 140 may be configured to act as an input device of the headset 10. A user may transmit a sound or a control command to a processor 101 of the headset 10 through the microphone and control button module 140.

The main board 100 may be, for example, a ceramic substrate, a printed circuit board (PCB), an organic substrate, or an intermediate substrate, but the invention is not limited thereto. In this embodiment, the main board 100 may include the processor 101 and a transceiver 103.

The processor 101 may be, for example, a central processing unit (CPU) or other programmable microprocessor for general or special use, a digital signal processor (DSP), a programmable controller, an application specific integrated circuit (ASIC), or any other similar device or a combination of the foregoing devices. Nevertheless, the invention is not limited thereto.

To be more specific, the processor 101 may internally include one or plural processing units featuring different functions. As shown in FIG. 2, the processor 101 may include a data processing unit P1 and an audio processing unit P2, and the data processing unit P1 is coupled between a motion sensor 111 and the audio processing unit P2. The data processing unit P1 may be configured to identify a posture of the user of the headset 10, and the audio processing unit P2 may be configured to execute audio processing and transmit audio data to a speaker 113 and/or a speaker 123.

The transceiver 103 is coupled the data processing unit P1 of the processor 101 and performs data transmission with the processor 101 or with an external device through a wired or wireless manner. The transceiver 103 may also execute, for example, low noise amplifying (LNA), impedance matching, frequency mixing, frequency up/down-conversion, filtering, amplifying, and other related operations.

The first housing 110 corresponds to a first ear of the user of the headset 10, and the motion sensor 111 and the speaker 113 may be disposed at the first housing 110. The second housing 120 corresponds to a second ear of the user of the headset 10, and a physiological sensor 121 and the speaker 123 may be disposed at the second housing 120. The speaker 113 and the speaker 123 are both coupled to the audio processing unit P2 of the processor 101. The audio processing unit P2 may transmit a signal b to the speaker 113 and/or the speaker 123, so as to play the audio data through the speaker 113 and/or the speaker 123. In some embodiments, the motion sensor 111 and/or the physiological sensor 121 may be disposed at the first housing 110, and the motion sensor 111 and/or the physiological sensor 121 may be disposed at the second housing 120. The invention is not limited thereto.

The motion sensor 111 is coupled to the data processing unit P1 of the processor 101 and may be configured to sense the posture of the user of the headset 10 to generate sensing data d1. The motion sensor 111 may be, for example, an electronic compass, a geomagnetic sensor, a gyroscope, an angular velocity detector, an acceleration sensor, a six-axis sensor, or a nine-axis sensor, but the invention is not limited thereto. The sensing data d1 may be a movement posture parameter associated with human postures such as displacement, acceleration, angular velocity, or magnetic changes.

The physiological sensor 121 is coupled to the data processing unit P1 of the processor 101 and may be configured to sense physiological information of the user of the headset 10 to generate sensing data d2. The physiological sensor 121 may be, for example, an electrocardiogram sensor, a voice sensor, a temperature and humidity sensor, a sweat pH level sensor, or an electromyography sensor, but the invention is not limited thereto. The sensing data d2 may be a physiological parameter associated with a physiological condition of a human body such as a heart rate, a respiratory rate, or an allergic response.

The headset 10 may include a general mode and a training mode. In a general mode, the headset 10 may be configured to identify the posture of the user and generate an output result op configured to determine whether the posture of the user is correct. Herein, the transceiver 103 of the headset 10 does not transmit any data other than the output result op. In other words, the headset 10 consumes merely a considerably small amount of power in the general mode.

From another perspective, in the training mode, the headset 10 may use the sensing data generated when the user is in motion to train an identification model im. To be more specific, in the training mode, the data processing unit P1 of the headset 10 may transmit the sensing data d1 and/or the sensing data d2 to the external device (e.g., a smartphone) through the transceiver 103. The external device may train the identification model im according to the sensing data d1 and/or the sensing data d2. In other words, the training mode of the headset 10 may generate training data associated with the posture or physiological information of the user.

In the general mode, the data processing unit P1 of the processor 101 may receive the sensing data d1 from the motion sensor 111 and determines whether the posture of the user of the headset 10 is correct according to the sensing data d1, so as to generate the output result op. The output result op may be configured to remind the user that the posture is correct or incorrect when the user is in motion.

To be more specific, the data processing unit P1 of the processor 101 may store (or pre-store) one or a plurality of the identification models im. The data processing unit P1 may determine whether the posture of the user is correct according to the identification model im and the sensing data d1 and generates the output result op. In some embodiments, the data processing unit P1 may further determines whether the posture of the user is correct according to the identification model im, the sensing data d1, and the sensing data d2 and generates the output result op.

After the output result op is generated, the data processing unit P1 may transmit the output result op to the external device (e.g., a smartphone) through the transceiver 103. From another perspective, the data processing unit P1 may also transmit the output result op to the audio processing unit P2. The audio processing unit P2 may perform audio processing to the output result op to generate the corresponding signal b and transmits the signal b to the speaker 113 and the speaker 123 for playing. The signal b may remind the user of the headset 10 that whether his/her posture is correct in a form of a reminder sound. When the signal b associated with the output result op is played, if the user is using the headset 10 to listen to the music or radio or other audio data, the audio processing unit P2 turns down volume of the audio data currently being played. Accordingly, the user may hear the reminder sound corresponding to the signal b more clearly.

In some embodiments, the data processing unit P1 of the processor 101 may receive a workout menu set by the user through the transceiver 103. For instance, the user may set the workout menu through a smartphone app and transmits the workout menu to the headset 10. The data processing unit P1 of the processor 101 may determine whether the posture of the user is correct according to the sensing data d1, the identification model im, and the workout menu, so as to generate the output result op. The workout menu may include a workout type, a workout set, or a workout rep, but the invention is not limited thereto.

In some embodiments, in addition to using the identification model im preset in the data processing unit P1 to identify the posture, the headset 10 may also receive a new identification model im from the external device. Specifically, the data processing unit P1 of the processor 101 may receive an update message from the transceiver 103. Herein, the update message is configured remind the headset 10 to perform a firmware update, and the update message may include information related to the identification model im. The data processing unit P1 may update firmware of the headset 10 in response to the received update message, so as to obtain an updated or added identification model im.

Figure 3:
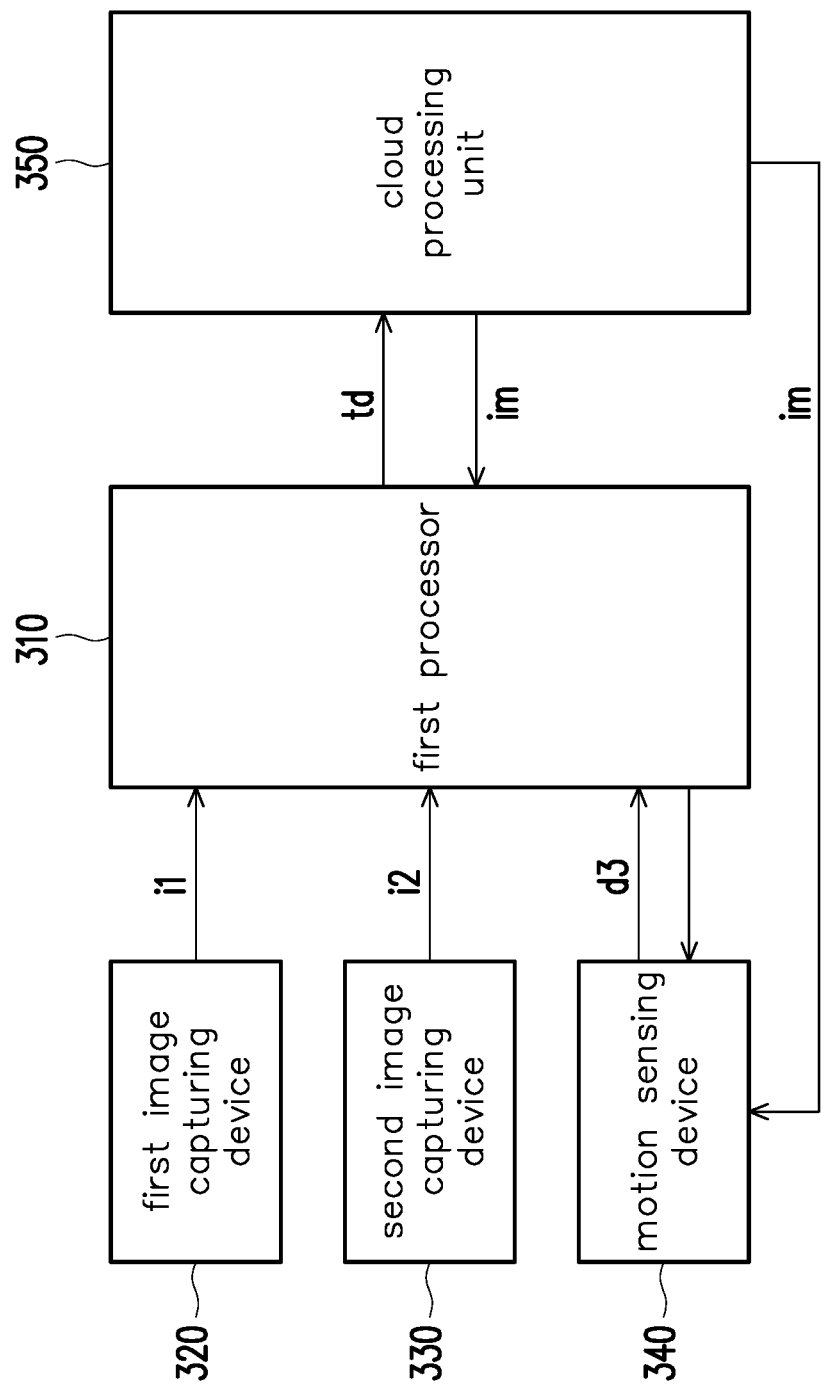
FIG. 3 is a schematic diagram illustrating a system for generating label data according to an embodiment of the invention.

FIG. 3 is a schematic diagram illustrating a system 30 for generating label data according to an embodiment of the invention. The system 30 may include a first processor 310, a first image capturing device 320, a second image capturing device 330, a motion sensing device 340, and a cloud processing unit 350. According to a posture of a user, the system 30 may be configured to automatically generate label data corresponding to the posture. The cloud processing unit 350 may be configured to use the label data to train a customized identification model corresponding to the posture of the user, so as to more accurately identify whether the posture of the user is correct when the user is in motion.

The first processor 310 is coupled to the first image capturing device 320, the second image capturing device 330, the motion sensing device 340, and the cloud processing unit 350. The first processor 310 may be, for example, a central processing unit or other programmable microprocessor for general or special use, a digital signal processor, a programmable controller, an application specific integrated circuit, or any other similar device or a combination of the foregoing devices, but the invention is not limited thereto.

The first image capturing device 320 may sense the posture of the user to generate a non-depth image i1 corresponding to the posture. The second image capturing device 330 may sense the posture of the user to generate a depth image i2 corresponding to the posture. The first image capturing device 320 and the second image capturing device 330 may be, for example, cameras, video cameras, etc., but the invention is not limited thereto. In some embodiments, the first image capturing device 320 may be, for example, a RGB video camera, the second image capturing device 330 may be, for example, a depth video camera, but the invention is not limited thereto.

The motion sensing device 340 may sense the posture of the user to generate motion data d3 corresponding to the posture. The motion sensing device 340 may be, for example, a six-axis sensor or a nine-axis sensor. In some embodiments, the motion sensing device 340 may be, for example, the headset 10 shown in FIG. 2, the motion data d3 may be, for example, the sensing data d1 shown in FIG. 2, but the invention is not limited thereto.

The cloud processing unit 350 is coupled to the first processor 310. The cloud processing unit 350 may be, for example, a central processing unit or other programmable microprocessor for general or special use, a digital signal processor, a programmable controller, an application specific integrated circuit, or any other similar device or a combination of the foregoing devices, but the invention is not limited thereto.

In this embodiment, when the user is in motion, the first processor 310 may receive the non-depth image i1 and the depth image i2 corresponding to the posture of the user respectively from the first image capturing device 320 and the second image capturing device 330 and receives the motion data d3 corresponding to the posture of the user from the motion sensing device 340. Next, the first processor 310 may identify the posture of the user based on the non-depth image i1 and the depth image i2 (e.g., identify the posture of the user through a preset or received identification model), so as to generate an identifying result corresponding to the posture of the user. After obtaining the identifying result, the first processor 310 may label the motion data d3 to generate corresponding label data td according to the identification result, and the label data td is the motion data d3 with a time label.

To be more specific, the first processor 310 may first detect a specific posture of the user in motion and start time of the specific posture according to the non-depth image i1 and the depth image i2 and then labels the motion data d3, so as to associate a start time label corresponding to the start time with the motion data d3. Next, the first processor 310 may detect end time of the specific posture according to the non-depth image i1 and the depth image i2 and labels the motion data d3, so as to associate an end time label corresponding to the end time with the motion data d3. After the start time label and the end time label are generated, the first processor 310 may label the motion data d3 at a time interval between the start time and the end time according to the start time label and the end time label, so that the motion data d3 at the time interval corresponds to the specific posture. That is, the first processor 310 associates a posture label corresponding to the specific posture with the motion data d3 at the time interval. After the foregoing steps are completed, the first processor 310 may generate the label data td, and the label data td is the labeled motion data d3.

After generating the label data td, the first processor 310 may transmit the label data td to the cloud processing unit 350. For instance, the first processor 310 may transmit the label data td corresponding to a user to the cloud processing unit 350 through a transmitter. The cloud processing unit 350 may train a corresponding identification model im based on the label data td, and the identification model im is configured to identify whether the posture of the user is correct. The cloud processing unit 350 may transmit the generated new or updated identification model im to the first processor 310, so that the first processor 310 may generate new label data according to the new identification model im.

From another perspective, the cloud processing unit 350 may transmit the generated identification model im to the motion sensing device 340. The motion sensing device 340 may determine whether the posture of the user in motion is correct or incorrect according to the received identification model im. Specifically, the cloud processing unit 350 may transmit an update message including information of the identification model im to the motion sensing device 340 in response to the generated identification model im. Herein, the update message is configured to remind the motion sensing device 340 to perform an update on firmware. The motion sensing device 340 may receive the update message from the cloud processing unit 350 and updates the firmware of the motion sensing device 340 according to the update message, so as to obtain an updated or a new identification model im.

Figure 4:
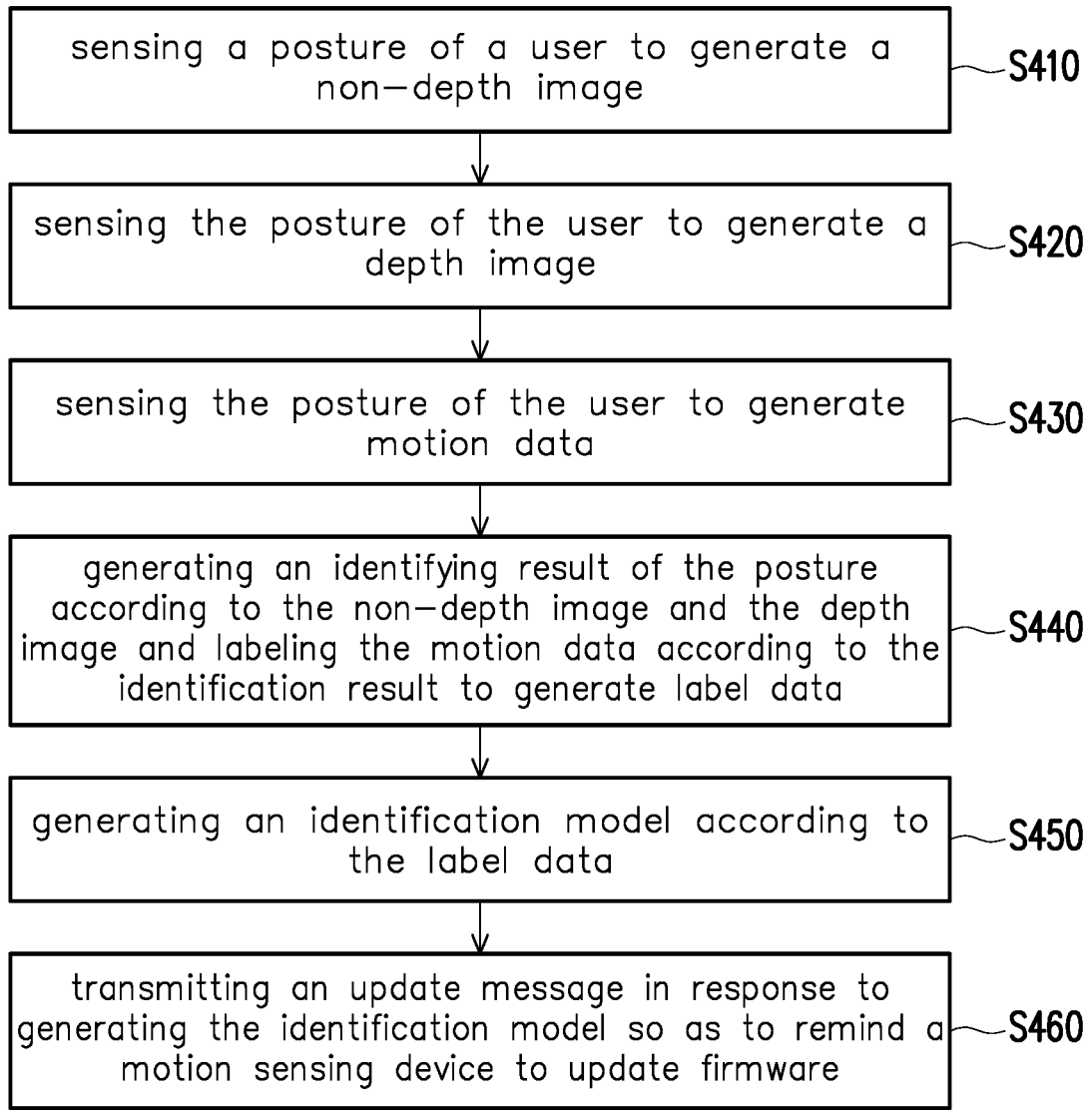
FIG. 4 is a flow chart illustrating a method for generating label data according to an embodiment of the invention.

FIG. 4 is a flow chart illustrating a method 40 for generating label data according to an embodiment of the invention. Herein, the method 40 may be implemented through the system 30 shown in FIG. 3. In step S410, a posture of a user is sensed to generate a non-depth image. In step S420, the posture of the user is sensed to generate a depth image. In step S430, the posture of the user is sensed to generate motion data. In step S440, an identifying result of the posture is generated according to the non-depth image and the depth image, and the motion data is labeled according to the identification result to generate label data. In step S450, an identification model is generated according to the label data. In step S460, an update message is transmitted in response to generating the identification model, so a motion sensing device is reminded to update firmware.

Figure 5:
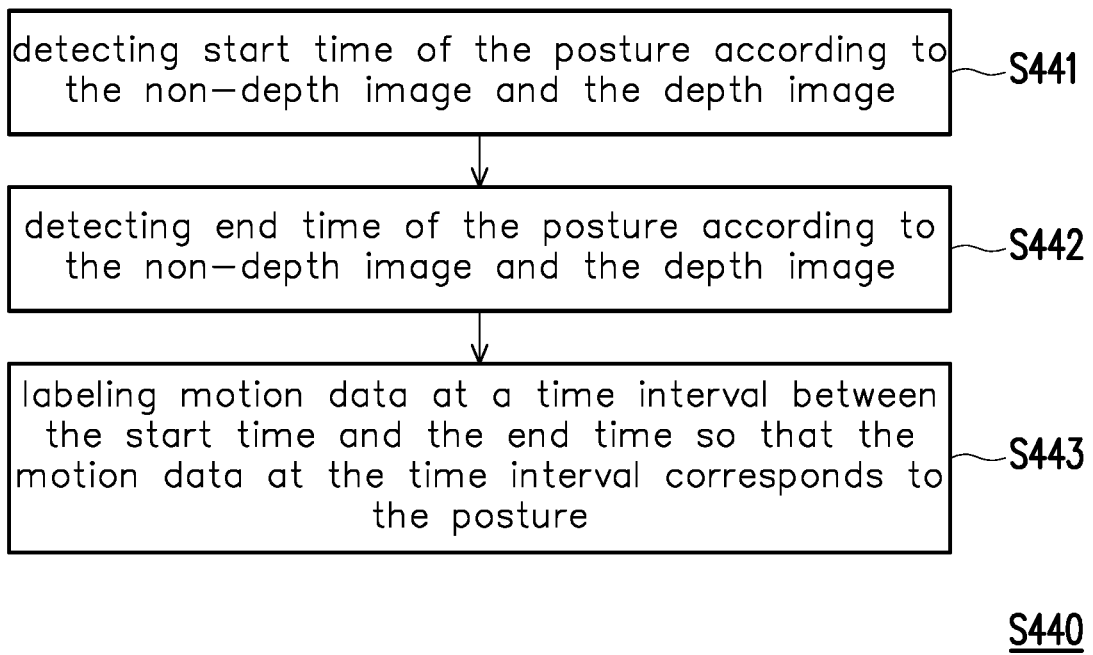
FIG. 5 is a flow chart further illustrating the step of the method for generating label data according to an embodiment of the invention.

FIG. 5 is a flow chart further illustrating step S440 of the method 40 for generating label data according to an embodiment of the invention. In step S441, start time of the posture is detected according to the non-depth image and the depth image. In step S442, end time of the posture is detected according to the non-depth image and the depth image. In step S443, motion data at a time interval between the start time and the end time is labeled, so that the motion data at the time interval corresponds to the posture.

In view of the foregoing, the headset provided by the invention may locally identify the posture and generates the identification result. The headset is capable of transmitting original data generated by the sensor to the external device such as a smartphone and the like without the use of wireless transmission technology. In this way, power consumed by the headset and/or the external device is significantly lowered. In addition, different types of sensors may be disposed at the headset to generate different types of sensing data, so that applications of the sensing data may be more diversified. From another perspective, the system for generating label data provided by the invention identifies the motion posture of the user by using the image processing technology and automatically labels the data according to the identifying result. The system for generating label data requires no human intervention in the process of generating the label data. In this way, the system may help the user to generate the label data more quickly, and moreover, identification accuracy of the identification model trained by using the label data is increased as well.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:
1. A headset, comprising:
a speaker, playing audio data;
a motion sensor, sensing a posture of a user to generate first sensing data;
a transceiver, performing data transmission with an external device; and
a processor, coupled to the motion sensor and the transceiver, the processor determines whether the posture is correct according to the first sensing data to generate an output result and transmits the output result through the transceiver,
wherein the output result indicates that the posture is correct or the posture is incorrect, and the headset comprises the following modes:
a general mode, the transceiver does not transmit any data other than the output result; and
a training mode, the transceiver transmits the first sensing data to the external device.

2. The headset as claimed in claim 1, wherein the processor stores a plurality of identification models and determines whether the posture is correct according to the first sensing data and the identification models to generate the output result.

3. The headset as claimed in claim 1, further comprising:
a physiological sensor, coupled to the processor, the physiological sensor sensing physiological information of the user to generate second sensing data, wherein the processor generates the output result according to the first sensing data and the second sensing data.

4. The headset as claimed in claim 3, further comprising:
a first housing, corresponding to a first ear of the user, wherein the motion sensor is disposed at the first housing; and
a second housing, corresponding to a second ear of the user, wherein the physiological sensor is disposed at the second housing.

5. The headset as claimed in claim 3, wherein the first sensing data is a movement posture parameter, and the second sensing data is a physiological parameter.

6. The headset as claimed in claim 1, wherein the processor turns down volume of the audio data currently being played and transmits a reminder sound associated with the output result to the speaker after the output result is generated.

7. The headset as claimed in claim 1, wherein the processor receives a workout menu set by an app through the transceiver and determines whether the posture is correct according to the first sensing data and the workout menu to generate the output result, wherein the workout menu comprises at least one of a workout type, a workout set, and a workout rep.

8. The headset as claimed in claim 1, wherein the processor updates firmware in response to an update message received by the transceiver so as to obtain the updated identification models.

9. A headset, comprising:
a speaker, playing audio data;
a motion sensor, sensing a posture of a user to generate first sensing data; and
a processor, comprising a data processing unit and an audio processing unit, the data processing unit coupled between the motion sensor and the audio processing unit, determining whether the posture is correct according to the first sensing data to generate an output result, transmitting the output result to the speaker for playing through the audio processing unit,
wherein the output result indicates that the posture is correct or the posture is incorrect, and the headset comprises the following modes:

a general mode, the audio processing unit transmits a reminder sound associated with the output result to the speaker after the data processing unit generates the output result; and a training mode, the data processing unit transmits the first sensing data to an external device.

10. The headset as claimed in claim 9, wherein the data processing unit stores a plurality of identification models and determines whether the posture is correct according to the first sensing data and the identification models to generate the output result.

11. The headset as claimed in claim 10, wherein the headset further comprises a transceiver, the transceiver is coupled to the data processing unit and performs data transmission with an external device, and the data processing unit updates firmware in response to an update message received by the transceiver so as to obtain the updated identification models.

12. The headset as claimed in claim 9, wherein the audio processing unit turns down volume of the audio data currently being played and transmits the reminder sound associated with the output result to the speaker after the data processing unit generates the output result in the general mode.

* * * * *